(12) United States Patent
Dambmann et al.

(10) Patent No.: US 7,560,127 B2
(45) Date of Patent: Jul. 14, 2009

(54) CHEESE MAKING PROCESS

(75) Inventors: Claus Dambmann, Søborg (DK); Peter Budtz, Frederiksberg (DK); Per Munk Nielsen, Hillerød (DK)

(73) Assignee: DSM IP Assets B.V., Heerlen (NL)

( * ) Notice: Subject to any disclaimer, the term of this patent is extended or adjusted under 35 U.S.C. 154(b) by 492 days.

(21) Appl. No.: 10/471,882

(22) PCT Filed: Mar. 21, 2002

(86) PCT No.: PCT/EP02/03341

§ 371 (c)(1),
(2), (4) Date: Mar. 12, 2004

(87) PCT Pub. No.: WO02/074097

PCT Pub. Date: Sep. 26, 2002

(65) Prior Publication Data

US 2004/0146603 A1    Jul. 29, 2004

(30) Foreign Application Priority Data

Mar. 21, 2001 (EP) .................................. 01000063

(51) Int. Cl.
*A23C 9/12* (2006.01)

(52) U.S. Cl. ............................. 426/36; 426/34; 426/582

(58) Field of Classification Search ................... 426/34, 426/36, 38, 40, 42, 43, 580, 582
See application file for complete search history.

(56) References Cited

U.S. PATENT DOCUMENTS

| 4,925,680 A | 5/1990 | Schweikhardt et al. ......... 426/42 |
| 7,041,323 B2 * | 5/2006 | Andersen ..................... 426/38 |

FOREIGN PATENT DOCUMENTS

| GB | 1123647 | 8/1968 |
| WO | WO 99/08511 | 2/1999 |

OTHER PUBLICATIONS

International Search Report mailed on Jul. 19, 2002, for PCT patent application No. PCT/EP02/03341 filed on Mar. 21, 2002, 3 pages.
Minkiewicz, Polish Journal of Food and Nutrition Sciences (1993) 2(3):39-48.
Unstunol et al., Journal of Dairy Science (1990) 73(1):17-25.

* cited by examiner

*Primary Examiner*—Leslie Wong
(74) *Attorney, Agent, or Firm*—Nixon & Vanderhye P.C.

(57) ABSTRACT

The present invention describes a process for making cheese, comprising: a) adding to milk a carbohydrase selected from the group consisting of α-galactosidase, N-acetyl-galactosaminidase and neuraminidase, b) incubating so as to partially deglycosylate κ-casein in the milk, and c) during or after step b) conditions causing clotting of the milk.

Figure 1:
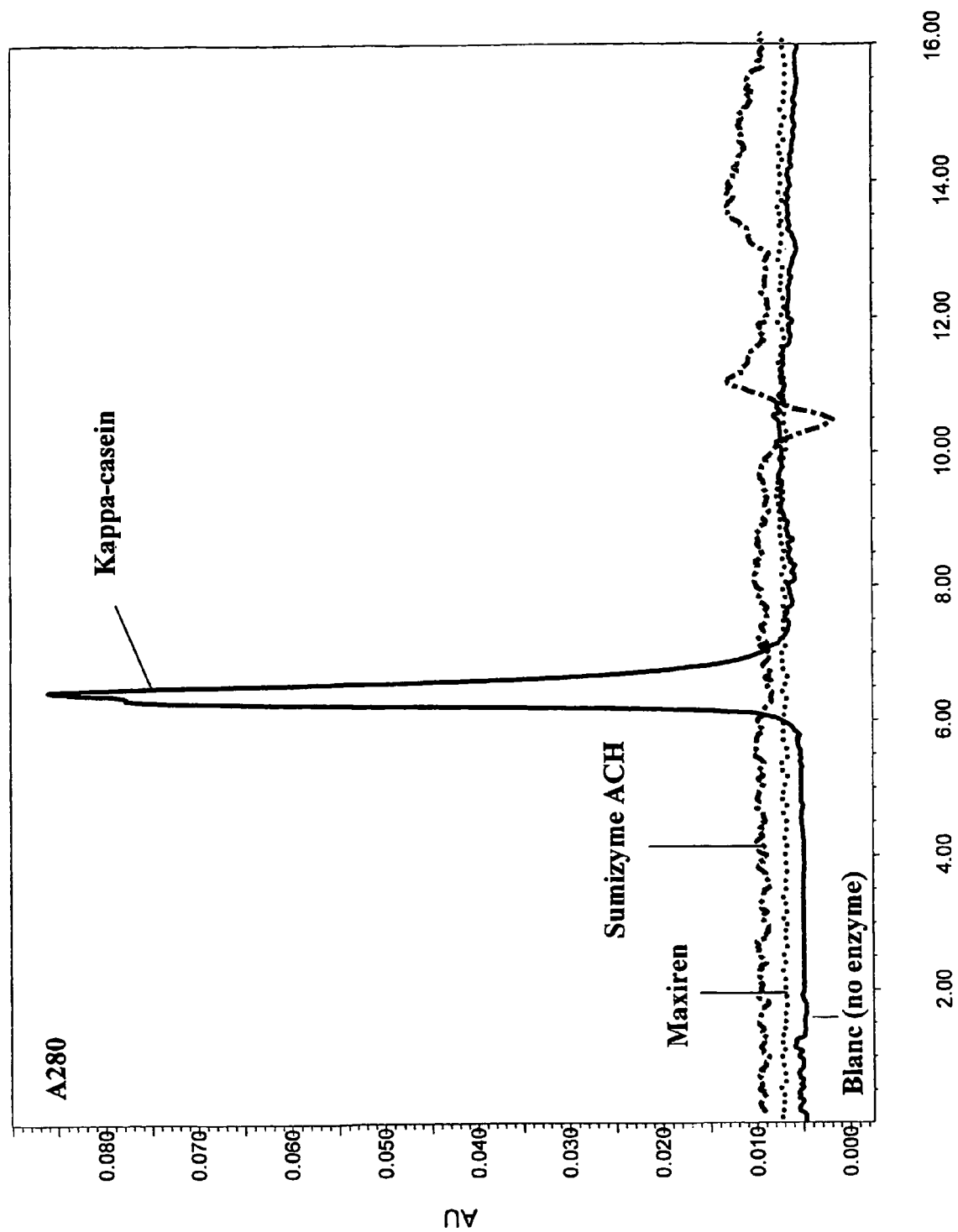

21 Claims, 1 Drawing Sheet

CHEESE MAKING PROCESS

CROSS REFERENCE TO RELATED APPLICATIONS

This application is the national phase of PCT application PCT/EP02/03341 having an international filing date of 21 Mar. 2002, and claims priority from European application EP 01000063.6 filed 21 Mar. 2001. The contents of these documents are incorporated herein by reference

TECHNICAL FIELD

This invention relates to a cheese-making process.

BACKGROUND ART

In the production of cheese it is necessary to coagulate the cheese-milk to be able to separate the cheese-matters e.g. casein from the whey. Products containing the proteolytic enzyme chymosin, which is a milk-coagulating enzyme isolated from the fourth stomach of calf, have for many years been used for this purpose. Shortage of calf stomachs has in the last decades resulted in intense research for other milk-coagulating enzymes. Today also bovine pepsin, porcine pepsin as well as microbial enzymes are used commercially. All these known milk-clotting enzymes are characterized by having specificity for the peptide bond between residues 105 (phenylalanine) and 106 (methionine) or a bond adjacent to that in κ-casein. This means that by employing these enzymes in cheese-making, the κ-casein is split at the junction between para-κ-casein and the macro-peptide moiety called glyco-macro-peptide (GMP) carrying the negative charges. When this occurs the macro-peptide diffuses into the whey, its stabilizing effect on the casein micelles is lost, and the casein micelles can start to aggregate once sufficient of their κ-casein has been hydrolysed. For further elaboration on the enzymatic coagulation of milk see e.g. D. G. Dalgleish in *Advanced Dairy Chemistry* vol 1 ed by P. F. Fox Elsevier, London, 1992.

It is an object of this invention to provide a novel cheese-making process using a different enzyme from known methods. It is also an object of the invention to provide a method having a higher cheese yield.

SUMMARY OF THE INVENTION

In this invention it is surprisingly found that it is not necessary to hydrolyse the peptide bond between residue 105 phenylalanine and residue 106 methionine or a bond adjacent to that in κ-casein to effect clotting of cheese-milk. It was surprisingly found that a deglycosylation of κ-casein will lead to clotting as it are the sugars associated with κ-casein that carry the negative charge which stabilise the casein micelles. Clotting of the milk in this way results in a process in which a larger part of the κ-casein is retained in the cheese and a higher yield can be obtained than using proteolytic activity of chymosin.

Accordingly, the invention provides a novel process for making cheese, comprising:
  a) adding to milk a carbohydrase selected from the group consisting of α-galactosidase, N-acetyl-galactosaminidase and neuraminidase,
  b) incubating so as to partially deglycosylate κ-casein in the milk, and
  c) during or after step b) conditions causing clotting of the milk.

The novel method, described in the invention, will also lead to higher cheese yield as compared to the traditional cheese making processes in which the clotting is the result of proteolytic activity of enzymes like chymosin.

DETAILED DISCLOSURE OF THE INVENTION

Cheesemaking

Any type of milk, in particular milk from ruminants such as cows, sheep, goats, buffalos or camels, may be used as the starting material in the process of the invention, e.g. as reconstituted milk, whole milk, concentrated whole milk or low fat milk. The milk may be concentrated in various ways such as by evaporation or spray-drying, but is preferably concentrated by membrane-filtration, i.e. ultra-filtration in which molecules with a molecular weight of up to 20,000 Dalton are allowed to pass the membrane, optionally with dia-filtration before or after ultra-filtration in which molecules of a molecular weight of up to 500 Dalton are allowed to pass the membrane. For a more detailed description of the ultra-filtration process, see for instance Quist et al., *Beretning fra Statens Meieriforsøg*, 1986.

A starter culture may be added to the milk before or simultaneously with the addition of the coagulation inducing enzyme described in the present invention. The starter culture is a culture of lactic acid bacteria used, in conventional cheese-making, to ferment the lactose present in the milk and to cause further decomposition of the clotted casein into smaller peptides and free amino acids as a result of their production of proteases and peptidases. The starter culture may be added in amounts which are conventional for the present purpose, i.e. typically amounts of about 1 *E4 to 1 *E5 bacteria/g of cheese-milk, and may be added in the form of freeze-dried, frozen or liquid cultures. When the milk employed in the process of the invention is concentrated milk, it is preferred to add the starter-culture after concentrating the milk, although this is not an absolute requirement, as the starter-culture bacteria will be retained during filtration.

After adding the enzyme giving cause to clotting as described in the present invention the subsequent steps in the cheese-making process, i.e. further salting, pressing, and ripening of the curd, may be conducted in the traditional way of producing cheese, e.g. as described by R. Scott, *Cheesemaking in Practice*, 2nd Ed., Elsevier, London, 1986.

It is at present contemplated that cheese may advantageously be prepared by the process of the invention with increased cheese yield, compared to the traditional processes in which proteolytic enzymes are used. This is of significant economic and industrial interest. The expected increase in cheese yield can be approximated as follows. Caseins are the major protein components that make up the cheese matrix; globular milk proteins like β-lactoglobulin are retained in the whey during the cheese making process. Caseins are present in milk in the following concentrations expressed as grams per 100 g dry protein: $\alpha_{S1}$ 31, $\alpha_{S2}$ 8, β 28, κ 10, γ 2.4 (for reference see: Walstra et al, (1999) Dairy technology, pages 80-81, Marcel Dekker Inc., New York). Coagulation during cheese making is initiated by proteolytic cleavage of a specific bond in κ-casein (molecular weight 19.5 kDalton), leading to the formation of two smaller proteins: para-κ-casein (MW 12.5 kDalton) that is included in the cheese matrix and the glyco-macro-peptide (GMP, 7 kDalton) that is lost in the whey. When deglycosylation of κ-casein is used to initiate the coagulation process instead of the proteolytic cleavage by e.g. chymosin, the GMP is not cleaved off and is therefore not lost in the whey but is retained in the cheese matrix. This would increase the amount of casein protein included in the cheese matrix by 4.7% for the deglycosylation process as compared to the proteolytic process. This, in turn, will lead to an increase in cheese yield. The actual increase in cheese yield will of course depend on factors like processing conditions and composition of the cheese milk and is difficult to predict exactly.

Carbohydrase

The carbohydrase used in the process of the invention is an α-galactosidase, a galactosaminidase or a neuraminidase.

α-galactosidase (EC 3.2.1.22) may be derived from an Aspergillus species like a strain of *Aspergillus niger* or *Aspergillus aculeatus*. One example is the commercial product Alpha-Gal (product of Novo Nordisk A/S), another example in the commercial product Sumizyme ACH (product of Shin Nihon Co., Ltd.)

N-acetyl-galactosaminidase may be α-N-acetylgalactosaminidase (EC 3.2.1.49) or β-N-acetylgalactosaminidase (EC 3.2.1.53). It may be derived from jack beans (*Canavalia ensiformis*). Neuraminidase (EC 3.2.1.18) may be derived from a strain of *Clostridium perfringens*.

In a preferred embodiment, two or three of the above enzyme activities are used together to remove more carbohydrate from the κ-casein. Typical reaction conditions are 5-30 minutes at 20-40° C.

LEGEND TO THE FIGURE

FIG. 1: Overlaid and back ground corrected chromatograms of the clear supernatants of the κ-casein-solutions after incubation with Maxiren, Sumizyme ACH or without enzyme additions. For experimental details, see text of example 5.

EXAMPLE 1

Miniature cheeses were produced as described by Shakeel-Ur-Rehman et al. (Protocol for the manufacture of miniature cheeses in Lait, 78 (1998), 607-620). Raw cows milk was pasteurised by heating for 30 minutes at 63° C. The pasteurised milk was transferred to wide mouth plastic centrifuge bottles (200 ml per bottle) and cooled to 31° C. Subsequently, 0.72 ml of starter culture DS 5LT1 (D$M Gist B. V., Delft, The Netherlands) was added to each of the 200 ml of pasteurised milk in the centrifuge bottles and the milk was ripened for 20 minutes. Than, $CaCl_2$ (132 μl of a 1 mol.l$^{-1}$ solution per 200 ml ripened milk) was added, followed by addition of the coagulant (0.04 IMCU per ml). The milk solutions were held for 40-50 minutes at 31° C. until a coagulum was formed. The coagulum was cut manually by cutters of stretched wire, spaced 1 cm apart on a frame. Healing was allowed for 2 minutes followed by gently stirring for 10 minutes. After that, the temperature was increased gradually to 39° C. over 30 minutes under continuous stirring of the curd/whey mixture. Upon reaching a pH of 6.2 the curd/whey mixtures were centrifuged at room temperature for 60 minutes at 1,700 g. The whey was drained and the curds were held in a water bath at 36° C. The cheeses were inverted every 15 minutes until the pH had decreased to 5.2-5.3 and were then centrifuged at room temperature at 1,700 g for 20 minutes. After further whey drainage the cheeses were weighed. The cheese yield was calculated as follows:

Cheese yield (%)={(cheese weight)/(total milk weight)}*100%.

EXAMPLE 2

The milk clotting activity of the commercial *Aspergillus niger* derived α-galactosidase preparation Sumizyme ACH, (Shin Nihon Chemical Co., lot nr 91-1221) was determined in IMCU (International Milk Clotting Unit) according to the international IDF (International Dairy Federation) standard 157A:1997. The activity of the commercial α-galactosidase preparation was determined at 13.9 international milk-clotting units (IMCU) per gram of the product.

EXAMPLE 3

The a-specific proteolytic activity of the commercial α-galactosidase Sumizyme ACH was determined using two independent methods. Sumizyme ACH (lot nr. 91-1221) was dissolved to an end concentration of 25 mg/ml in buffer (20 mM $NaP_i$ containing 50 mM NaCl, pH7.0). In the first method, proteolytic activity was determined using casein resorufin labelled (obtained from Roche Applied Sciences) as the substrate. Proteolytic activity in 100 μl of the Sumizyme ACH sample was determined according to the method provided by the supplier of the labelled casein at pH7.0. No significant colour formation could be observed after incubation at 37° C. for 30 minutes, demonstrating the absence of any significant proteolytic activity in the Sumizyme ACH preparation under the assay conditions. In the second method, 8 μl of the Sumizyme ACH solution was spotted on a photographic gelatin film (AGFAPAN APX100, obtained from AGFA). The film was incubated in a moisture regulated compartment at 37° C. for 30 minutes. The absence of any clearing zones after rinsing the film with water indicated absence of significant proteolytic activity. Both protease assays failed to show any significant proteolytic activity in the Sumizyme ACH preparation.

EXAMPLE 4

Mini cheeses were produced using Sumizyme ACH (lot nr. 91-1221) according to the procedure described in example 1. The commercial rennet Maxiren (DSM Gist B V, Delft, The Netherlands) was used as the control. This rennet is known for its excellent cheese making properties showing good taste and high yields. Two independent experiments using different milk batches were performed for each coagulant. Experimental results are shown in table 1:

TABLE 1

Experimental results of the preparation of mini-cheeses in two independent experiments using Maxiren or Sumizyme ACH as the coagulant.

| | Cheese nr | Weight milk (grams) | Weight Cheese (grams) | Yield (%) | Average yield (%) | Standard deviation (%) |
|---|---|---|---|---|---|---|
| | | | Experiment 1 | | | |
| Maxiren | 1 | 205.67 | 24.98 | 12.146 | 12.14 | 0.25 |
| | 2 | 206.09 | 25.06 | 12.160 | | |
| | 3 | 204.72 | 24.10 | 11.772 | | |
| | 4 | 207.19 | 25.84 | 12.472 | | |
| Sumizyme ACH | 5 | 204.65 | 25.04 | 12.236 | 12.27 | 0.23 |
| | 6 | 205.92 | 25.09 | 12.184 | | |
| | 7 | 204.76 | 24.60 | 12.014 | | |
| | 8 | 204.82 | 25.90 | 12.645 | | |
| | | | Experiment 2 | | | |
| Maxiren | 8 | 205.35 | 27.42 | 13.353 | 13.11 | 0.24 |
| | 9 | 205.12 | 26.39 | 12.866 | | |
| Sumizyme ACH | 10 | 206.11 | 28.29 | 12.726 | 13.40 | 0.32 |
| | 11 | 205.49 | 26.88 | 13.081 | | |

The numbers in the table above show that cheese can be obtained in excellent yields using α-galactosidase (Sumizyme ACH) instead of chymosin (Maxiren). The cheese yield obtained with α-galactosidase is at least comparable to the yield obtained with the efficient and reknown coagulant chymosin. The cheese yields after deglycosylation tend to be higher than the ones obtained via proteolysis, suggesting improved cheese yield. A yield increase for the deglycosylation-route would be in line with theoretical calculations as described in the text of this invention.

EXAMPLE 5

Purified κ-casein (obtained from Sigma) was dissolved to an end concentration of 3.3 mg/ml in 20 mM Tris.HAc, pH 6.5. Separate solutions were prepared to which either α-galactosidase (Sumizyme ACH) or chymosin (Maxiren) were added, each to an end concentratrion of 0.04 IMCU/ml. In a control experiment no enzyme was added. The samples were incubated at 32° C. for 30 minutes. Precipitate was formed between 1-3 minutes after enzyme addition in all solutions except for the control experiment. Samples of 10 μl of the clear supernatants were subjected to HPLC size exclusion chromatograhy, using a TSK3000 column (obtained from TosoHaas) using a buffer containing 0.1M $NaP_i$ and 0.2M NaCl (pH7.0) as the eluent at a flow rate of 1.0 ml/minute and using UV detection (280 nm). Chromatograms were recorded for all three solutions. In case precipitate was formed this was removed from solution by centrifugation. Liquid Chromatography—Mass spectra (LC/MS) analyses were recorded for the supernatants as follows. LC/MS was performed using an ion trap mass spectrometer (LCQ classic, Thermoquest, Breda, The Netherlands) coupled to a P4000 pump (Thermoquest, Breda, the Netherlands) in characterising the κ-casein supernatant solutions. The peptides formed were separated using a PEPMAP $C_{18}$ 300A (MIC-15-03-C18-PM, LC Packings, Amsterdam, The Netherlands) column in combination with a gradient of 0.1% formic acid in Milli Q water (Millipore, Bedford, Mass., USA; solution A) and 0.1% formic acid in acetonitrile (solution B) for elution. The gradient started at 90% of solution A and increased to 40% of solution B in 45 minutes and was kept at the latter ratio for another 5 minutes. The injection volume used was 50 μl, the flow rate was 50 μl/min and the column temperature was maintained ambient. The protein concentration of the injected sample was approx. 50 μg/ml.

Detailed information on the individual peptides was obtained by using the "scan dependent" MS/MS algorithm, which is a characteristic algorithm for an ion trap mass spectrometer.

Full scan analysis was followed by zoom scan analysis for the determination of the charge state of the most intense ion in the full scan mass range. Subsequent MS/MS analysis of the latter ion resulted in partial peptide sequence information, which could be used for database searching using the SEQUEST application from Xcalibur Bioworks (Thermoquest, Breda, The Netherlands). Databanks used were extracted from the OWL.fasta databank, available at the NCBI (National Centre for Biotechnology informatics), containing bovine caseines only for this particular application.

Mass spectrometrix analysis of the clear supernatant solution after incubation with Maxiren showed a somewhat heterogeneous peak with a lower mass limit at approximately 6700 Dalton, most probably being the κ-casein derived GMP (residues nr. 106-169), but to large to identify by MS/MS fragmentation and database searching. After digestion of this peptide using the endo-protease endo Asp-N, only three peptides were generated, which could be identified to cover the κ-casein amino acid sequence 106-169, by using databank searching. This unambiguously identified the GMP in the supernatant solution.

The resulting chromatograms of the clear solutions, corrected for background, are shown in FIG. 1.

The blanc experiment shows a strong peak in the chromatogram for the intact κ-casein. After incubation with chymosin (Maxiren), the κ-casein peak has completely disappeared, indicating its quantitative precipitation. Mass spectrometric analysis of the clear supernatant solution after incubation with Maxiren showed a somewhat heterogeneous peak with a lower mass limit at approximately 6700 Dalton, most probably being the κ-casein derived GMP (residues nr. 106-169), but to large to identify by MS/MS fragmentation and database searching. After digestion of this peptide using the endo-protease endo Asp-N, only three peptides were generated, which could be identified to cover the κ-casein amino acid sequence 106-169, by using databank searching. This unambiguously identified the GMP in the supernatant solution.

After incubation of κ-casein with α-galactosidase (Sumizyme ACH), the κ-casein peak has completely disappeared, similar to what was observed for chymosin (see FIG. 1). In this case, however, the mass spectrometric analysis showed complete absence of the GMP in the supernatant, as expected. This example therefore shows that deglycosylation can be used to strongly reduce the solubility of κ-casein in aqueous solutions offering a route for enzyme mediated coagulation of κ-casein containing casein micelles resulting in cheese making (as described in example 4). The deglycosylation of κ-casein will obviously result in a higher amount of casein incorporation in the cheese compared to the chymosin (or other protease coagulants) mediated proteolytic process. Therefore, the novel cheese making process will give increased cheese yield with a theoretical maximum increase of 4.7%, the actual cheese yield depending on process parameters during the cheese making process.

The invention claimed is:

1. A process for making cheese, comprising:
   a) adding to milk at least one carbohydrase selected from the group consisting of α-galactosidase, N-acetyl-galactosaminidase and neuraminidase;
   b) incubating so as to partially deglycosylate κ-casein in the milk with the carbohydrase; and
   c) during or after step b) effecting clotting of the milk using the carbohydrase's partial deglycosylation of the κ-casein therein, wherein an enzyme capable of splitting κ-casein is not used for clotting.

2. The process of claim 1, wherein the clotting is done at a total calcium concentration above 4 mM.

3. The process of claim 1, further comprising adding lactic acid bacteria as a starter culture before or simultaneously with adding of the carbohydrase.

4. The process of claim 1, wherein the incubating is continued to 60-80% deglycosylation of κ-casein.

5. The process of claim 1, wherein the carbohydrase is an α-galactosidase derived from a strain of *Aspergillus*.

6. The process of claim 5, wherein the strain of *Aspergillus* is *Aspergillus niger*.

7. The process of claim 5, wherein the strain of *Aspergillus* is *Aspergillus aculeatus*.

8. The process of claim 1, wherein the carbohydrase is α or β-N- acetylgalactosaminidase.

9. The process of claim 1, wherein at least two carbohydrases are added.

10. The process of claim 1, wherein an increased cheese yield is obtained as compared to a cheese making process employing a proteolytic coagulant.

11. The process of claim 8, wherein the α or β-N-acetylgalactosaminidase is derived from jack beans (*Canavalia ensiformis*).

12. A process for making cheese, comprising:
   a) adding to milk at least α-galactosidase, N-acetyl-galactosaminidase or both in an amount to clot the milk by at least partially deglycosylating κ-casein therein, wherein an enzyme capable of splitting κ-casein is not used for clotting; and
   b) incubating so as to partially deglycosylate κ-casein in the milk and effect clotting.

13. The process of claim 12, wherein the clotting is done at a total calcium concentration above 4 mM.

14. The process of claim 12, further comprising adding lactic acid bacteria as a starter culture to the milk.

15. The process of claim 12, wherein the incubating is continued to 60-80% deglycosylation of κ-casein.

16. The process of claim 12, wherein the carbohydrase is an α-galactosidase derived from a strain of *Aspergillus*.

17. The process of claim 16, wherein the strain of *Aspergillus* is *Aspergillus niger* or *Aspergillus aculeatus*.

18. The process of claim 12, wherein the carbohydrase is α or β-N-acetylgalactosaminidase.

19. The process of claim 18, wherein the α or β-N-acetylgalactosaminidase is derived from jack beans (*Canavalia ensiformis*).

20. A process for clotting milk to make cheese, comprising:
   a) adding to milk at least one carbohydrase selected from the group consisting of α-galactosidase, N-acetyl-galactosaminidase and neuraminidase in an amount to clot the milk by deglycosylation of κ-casein therein, wherein an enzyme capable of splitting κ-casein is not used for clotting; and
   b) incubating to clot the milk by deglycosylation of the κ-casein which is retained in the cheese, wherein clotting is effected without proteolysis of the κ-casein and loss of glycomacropeptide (GMP) in whey.

21. The process of claim 1, wherein the carbohydrase is neuraminidase derived from a strain of *Clostridium perfringens*.

* * * * *